United States Patent [19]

Ducellier, deceased et al.

[11] Patent Number: 4,824,571
[45] Date of Patent: Apr. 25, 1989

[54] METHOD OF AND EQUIPMENT FOR ANAEROBIC DEGRADATION OF ORGANIC PRODUCTS

[75] Inventors: Gilbert Ducellier, deceased, late of Montpellier, France, by Lucienne Ducellier, legal representative, Michele Fabres nee Ducellier, Monique Goudet nee Ducellier, Colette Segonzac nee Ducellier, Renee Ducellier nee Richert, Veronique Ducellier, heirs; Andre Pavia, 408 Rue Valery Larbaud, 34100 Montpellier, France

[73] Assignees: Union Industrielle et D'Entreprise; Valorga; Andre Pavia; Lucienne Ducellier; Michele Fabres nee Ducellier; Monique Goudet nee Ducellier; Colette Segonzac nee Ducellier; Renee Ducellier nee Richert; Veronique Ducellier, all of France

[21] Appl. No.: 929,195

[22] PCT Filed: Mar. 5, 1985

[86] PCT No.: PCT/FR85/00042
§ 371 Date: Dec. 23, 1986
§ 102(e) Date: Dec. 23, 1986

[87] PCT Pub. No.: WO86/05200
PCT Pub. Date: Sep. 12, 1986

[51] Int. Cl.$^4$ ............... C02F 3/28; C12P 5/02
[52] U.S. Cl. .................... 210/603; 210/194; 210/614; 210/219; 210/220; 435/167; 435/267
[58] Field of Search ............... 210/603, 219, 194, 218, 210/629, 621, 630, 220, 614, 96.1; 48/197 A; 435/167, 267

[56] References Cited

U.S. PATENT DOCUMENTS

| 3,210,053 | 10/1965 | Boester | 210/629 |
| 3,808,123 | 4/1974 | Neel | 210/629 |
| 4,437,992 | 3/1984 | Saito et al. | 210/603 |
| 4,663,046 | 5/1987 | Feldkirchner | 210/629 |
| 4,780,415 | 10/1988 | Ducellier et al. | 435/267 |

FOREIGN PATENT DOCUMENTS

| 0074290 | 3/1983 | European Pat. Off. | 210/603 |
| 3306149 | 9/1983 | Fed. Rep. of Germany | 210/603 |

Primary Examiner—Benoit Castel
Attorney, Agent, or Firm—Steinberg & Raskin

[57] ABSTRACT

The present invention relates to a method and equipment for carrying out the degradation of various organic products or waste in an anaerobic medium. The equipment comprises a plurality of ducts for reinjecting biogas into a fermentation vat sidewise spaced from each other and disposed at least in the major part of the vat, the duct being fed with biogas individually or in groups through independent valves so as to subdivide the fermentation vat into sectors independently fed with biogas. Preferably, a container is provided for storing biogas under pressure. These features lead to a simplification of the equipment and a decrease in the manufacturing costs.

26 Claims, 5 Drawing Sheets

Fig.1

METHOD OF AND EQUIPMENT FOR ANAEROBIC DEGRADATION OF ORGANIC PRODUCTS

BACKGROUND OF THE INVENTION

The present invention has for its object a method and an equipment for carrying out the degradation of organic products, by-products and scraps of human, animal or vegetable origin. More specifically, the subject matter of the invention is a process and an improved plant for performing a continuous methanizing of solid and/or liquid organic compounds.

In the European patent application EP-A-0074290 of the applicants, there has been described a method for carrying out a degradation in an anaerobic medium, for instance of methanogenesis of organic products, by-products or scraps of human, animal and/or vegetable origin, consisting in feeding the products to be degraded into a closed vessel after having possibly sowed the products with a suitable substrate, imposing upon the said products a direction of circulation within the vessel, recovering the gas produced called biogas evolved above the body of products and discharging the degraded products. This process describes various means for obtaining a pneumatic thrust of the substrate and a homogenization of the latter to accomplish a directed forced circulation and a good fluidizing thereof.

These means comprise feeding or discharging the products pneumatically preferably, through siphons by a pneumatic thrust; inducing sudden variations in pressure of the gas contained within the closed vessel in combination with a reintroduction of the biogas into the body of products present in the vessel.

In the method forming the subject matter of the European patent application EP-A-0074290, there has also been described a blowing of biogas by means of biref and successive jets through ducts opening into the bottom of the fermentation tank. Thus was carried out a simultaneous injection of gas into the whole bottom of the fermentation tank through the intermittent emission of brief jets. It appeared now during additional searches that this simultaneous blowing into the whole fermentation vat by means for time-bound short and successive jets did not lead to the desired result so that the fluidizing often was not perfect. It could moreover be found during these searches that the density of the substrate would vary from the feed shaft to the discharge shaft in such a manner that a uniform injection of biogas throughout the fermentation vat is inadequate because it does not at all take into account this difference in density.

SUMMARY OF THE INVENTION

The object of the present invention is therefore to remove the inconveniences of the method and the equipment forming the subject matter of this prior european application EP-A-0074290.

Thus, according to the present invention there is provided a method of the type previously described concerning the document EP-A-0074290, characterized in that one subdivides the vessel into a plurality of sectors; and in that one intermittently injects biogas into each one of the sectors under a pressure and for a period of time which are predetermined, adjustable in accordance with the density of the products within the sector.

Thus, according to the present invention, one adapts the biogas injection pressure and the duration of the injection in accordance with the instant density of the solid products or of the substrate within the injection sector. One therefore understands easily that one obtains with the invention a perfect fluidizing of the products during their circulation in the fermentation tank.

On the other hand, according to an advantageous characteristic of the method of the invention, one reintroduces biogas into each sector successively, that is in a manner shifted in time so as to obtain a rotation of the biogas injection within the vessel from one sector to another one. This rotation may be regular or irregular.

According to a particular characteristic of the method according to the invention, one provides a biogas storage tank under high pressure upstream of the fermentation vessel, the pressure being at least equal to the injection pressure in the sector where the density of the products is the highest one.

Likewise advantageously according to the method of the invention, the injection of biogas is programmed. This programmation may be performed by any means known to the man skilled in the art and in particular by a microprocessor or by a computer.

According to still another characteristic of the method of the invention constituting a particularly advantageous alternative embodiment, one effects a direct introduction of the products to be degraded into the vessel preferably towards the bottom of the vessel at a predetermined distance from the bottom. Preferably, this direct introduction is carried out by a mechanical thrust.

One thus obtains a simplification of the method and of the equipment while avoiding the presence of an inlet shaft which would compel to operating within the vessel at a pressure higher than atmospheric pressure.

In effect, with a direct introduction into the vessel according to the invention in particular through a mechanical thrust, it is possible to operate in an anerobic manner at the atmospheric pressure, thereby avoiding the extra costs due to the manufacture of vats capable of withstanding working pressures higher than 1 bar.

This mechanical thrust may be provided in a particularly simple manner by a pump for thick material which may preferably be of the piston or screw type.

According to still another characteristic of the method according to the invention, one performs a stirring with the biogas immediately at the inlet port of the products into the vessel.

The invention also relates to an equipment of the type described in EP-0074290 and characterized in that it comprises a plurality of ducts for the injection of biogas into the fermentation vessel or vat, which are sidewise spaced from each other and disposed at least in the major portion of the vat, the ducts being fed with biogas individually or in groups by independent valves so as to thus subdivide the fermentation vat in sectors independently fed with biogas.

According to an advantageous characteristic of the equipment according to the invention, the biogas injection circuit comprises a chest for storing biogas under pressure, wherein the biogas is stored until the obtainment of a pressure at least equal to the highest pressure required within the sectors of the vat.

According to the invention, each valve is provided so as to deliver a pressure which is a function of the density of the products within the associated sector.

The equipment according to the invention also comprises according to a preferred embodiment, a device for the programmed control of each valve of each sector.

According to another particularly advantageous embodiment of the equipment according to the invention, the latter comprises a biogas injection duct at the top of the fermentation vat provided with a suitable valve in order to provide a pneumatic thrust within the fermentation vat advantageously produced concurrently with the extraction of products from the fermentation vat for instance towards the discharge shaft.

According to another characteristic of the equipment according to the invention constituting a particularly advantageous alternative embodiment, the equipment comprises means for direct introduction of the products to be degraded into the vessel preferably towards the bottom of the vessel at a predetermined distance from the bottom. According a particular embodiment, these direct introduction means for comprise means providing a mechanical thrust, preferably comprising a pump for thick material.

According to a particular embodiment, this pump for thick material may be a piston pump or a screw pump.

According to still another characteristic of the equipment according to the invention, the latter comprises a connecting section at the inlet port of the vessel between the direct introduction means and the port proper, providing for fluid tightness.

According to another characteristic of the equipment according to the invention, the latter comprises biogas stirring means immediately at or in the vicinity of the port letting the products into the vessel.

According to another characteristic of the equipment according to the invention, the outlet of the degraded products from the vessel is a tangential outlet allowing an ejection through gravity.

According to still another characteristic of the equipment according to the invention, the latter comprises a divergent device at the inlet of the products, of suitable dimension so as to facilitate the ingress of the products into the fermentation vessel. Likewise it is preferred that the outlet be also fitted with a convergent device facilitating the egress of the fermented products or digestate.

BRIEF DESCRIPTION OF THE DRAWINGS

For a fuller understanding of the invention, reference is made to the following description, taken in conjunction with the accompanying drawings, in which.

DESCRIPTION OF THE PREFERRED EMBODIMENTS

Figure 1:
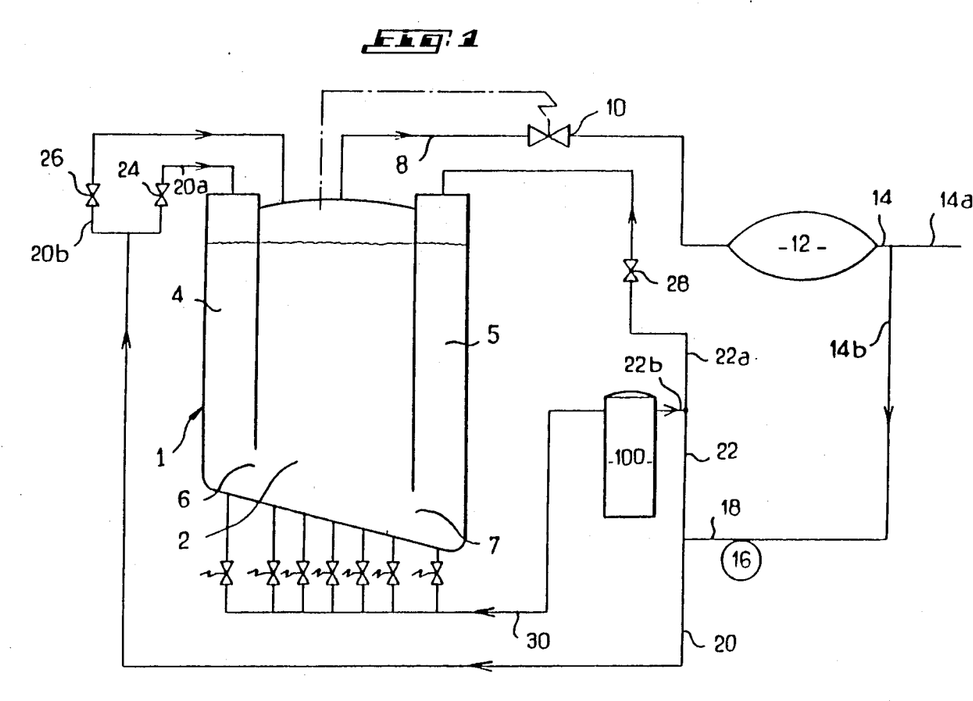
FIG. 1 diagrammatically illustrates an equipment showing in axial section the fermentation vat shown on FIG. 2 but with the products feed and discharge shafts in diametrally opposite relationship for more clarity whereas on FIG. 2, they are shown side by side.
Figure 2:
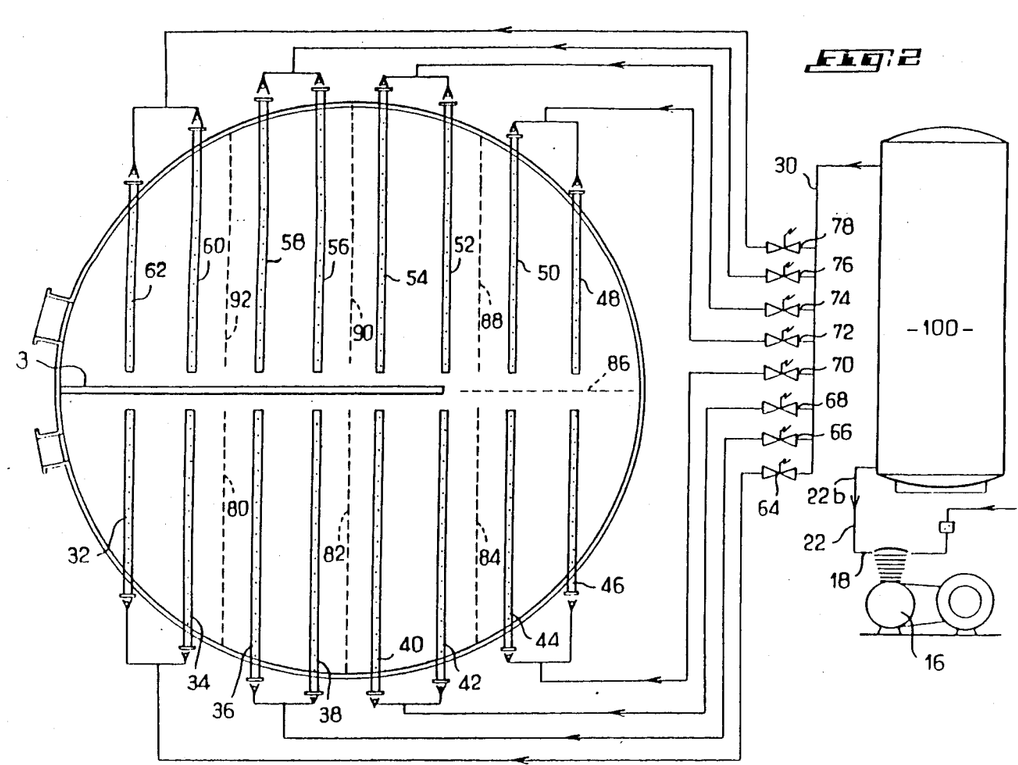
FIG. 2 shows a cross-section or top view of the bottom of the fermentation vat.

With reference to FIGS. 1 and 2, a plant according to the invention comprises a reactor 1 having an anaerobic fermentation vat 2 vertically divided by a transverse partition wall 3 into two parts, a first part being connected to a feed shaft 4 and a second part being connected to a discharge shaft 5 through a first siphon 6 and a second siphon 7, respectively, according to the European patent application EP-A-0074290.

This plant also comprises a gas or biogas outlet consisting of a duct 8 comprising a biogas discharge valve 10, the duct 8 being connected through the medium of a valve 10 to a container 12 forming a gasometer and the outlet 14 of which is subdivided into two ducts 14a and 14b, the duct 14a being connected to a biogas consumption device which for instance may be a burner, etc. The branched-off duct 14b is provided with a compressor 16 the outlet 18 of which is subdivided into several branch ducts 20, 22. The branch duct 20 is for instance feeding again through a subdivision to independent valves 24, 26 controlling the injection of the biogas towards the top of the feed shaft 4 and towards the top of the fermentation vat 2, respectively. The other branch duct 22 is in turn subdivided for feeding biogas directly from the compressor 16 through the branch duct 22a to the top of the discharge shaft 5 through the medium of a valve 28. Another subdivision 22b of the duct 22a is connected through a conduit 30 to a plurality of ducts which are clearly seen on FIG. 2 and numbered 32, 34, 36, 38, 40, 42, 44, 46, 48, 50, 52, 54, 56, 58, 60, 62, respectively, opening into the bottom of the fermentation vat 2 and consisting of tubes of suitable sections longitudinally provided with a plurality of injection ports. Each duct comprises an associated valve.

According to the present invention, this plurality of ducts 32 to 62 is fed with biogas individually or in groups (here two by two) as is well seen on FIG. 2, through independent valves 64, 66, 68, 70, 72, 74, 76, 78 so as to subdivide the vat into sectors independently fed with biogas. The sectors are symbolically embodied by the provision of dotted lines 80, 82, 84, 86, 88, 90, 92 which are well seen on FIG. 2. It should be noted that the ducts for reinjecting biogas into the vat are spaced sidewise from each other and disposed at least in the major portion of the vat, preferably in a regular manner as shown.

According to the present invention, each valve 64 to 78 is provided so as to deliver a pressure which is a function of the density of the products in the associated sector. On the other hand, each valve is operated preferably according to the invention by a programmed control device 130, so that one injects biogas intermittently into each one of the sectors of the vat 2 under a pressure and for a period of time which are predetermined, adjustable in relation to the density of the products within its associated sector.

Also according to an advantageous embodiment of the invention, the biogas injection circuit (ducts 22, 30) comprises a container 100 for storing biogas under pressure in which the biogas is stored until obtaining a pressure at least equal to the highest pressure required within one of the sectors of the vat 2.

With an injection pressure in accordance with the density of the products in a given sector, one means that the injection pressure is sufficient to produce a fluidizing of the mass of products having the said density.

It should be noted that the presence of his storage tank 100 for biogas under high pressure makes it possible in an unexpected manner to use a compressor 16 of low capacity, i.e. low coefficient of compression.

It should be noted furthermore that according to the invention, through the duct 20b for reinjection of biogas through the medium of the valve 26 one may produce a pneumatic thrust at the top of the vat 2 so as to remove the solid products circulating on the bottom of the reactor towards the discharge shaft 5.

It should also be noted that the valve 10 for discharging the biogas into the vat 2 is any valve whatsoever. It may be a hydraulically, pneumatically or electrically operated valve or even a hydraulic gate or valve.

Thus, this equipment allows carrying out the method stated previously, namely one obtains a subdivision of the vat or closed fermentation vessel into a plurality of sectors. With a view to provide a perfect or homogeneous fluidizing of the solid products or substrates within the vat 2, one injects biogas intermittently into each one of the sectors under a pressure and for a period of time which are predetermined, adjustable in relation to the density of the products within the associated sector.

Likewise, according to an advantageous characteristic of the invention, one injects biogas into each sector successively in a time-shifted manner so as to obtain a rotation of the biogas injection within the vessel from one sector to the other from the feed shaft 4 to the discharge shaft 5. Likewise, and owing to the programmation device, one obtains a programmed injection. This programmation may besides be automatically interlocked with means for detecting a lack of fluidity within one of the sectors of the vat so as to forthwith operate an injection into the said sector.

According to another characteristic of the invention, one effects the pneumatic thrust in the feed shaft 4 at the same time as the operation of the opening of the valve 10 for discharging the biogas produced in the vat 2 and one likewise effects the pneumatic thrust in the discharge shaft 5 at the same time as the biogas injection through the valve 26 at the top of the vat 2.

Thus, according to the invention, the obtainment of a practically perfect fluidizing of the products or substrates even with a high content of solid material such as manure or town refuse allows a simplification of the technology of manufacture of the bottom of the fermentation vat while permitting for instance to decrease the slope thereof thereby resulting in a lesser cost of the vat system.

On the other hand, one naturally obtains a better yield in biogas.

Figure 3:
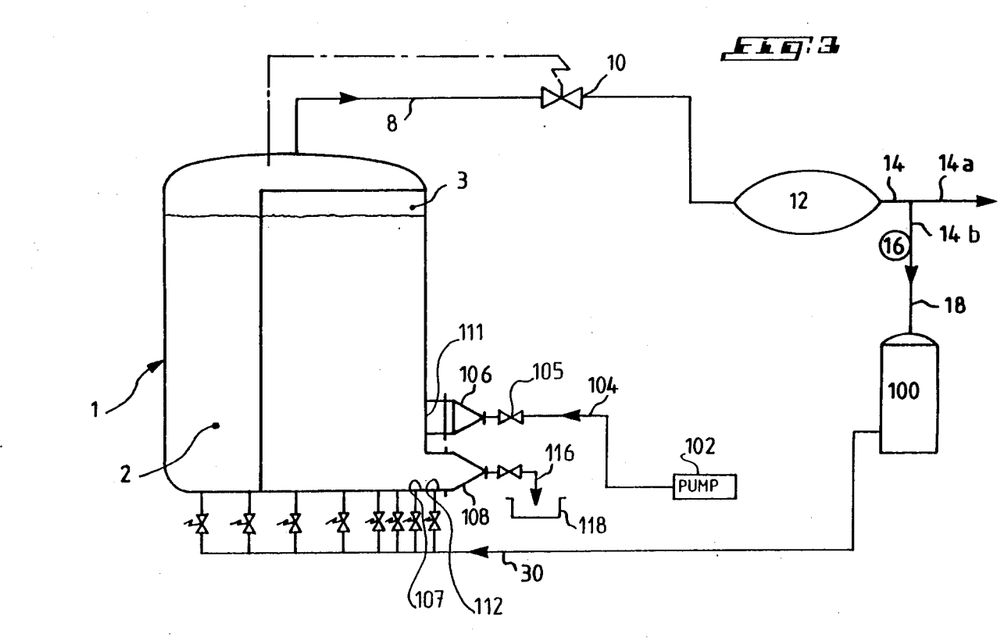
FIG. 3 shows a variant for the direct introduction of products into the vat.
Figure 4:
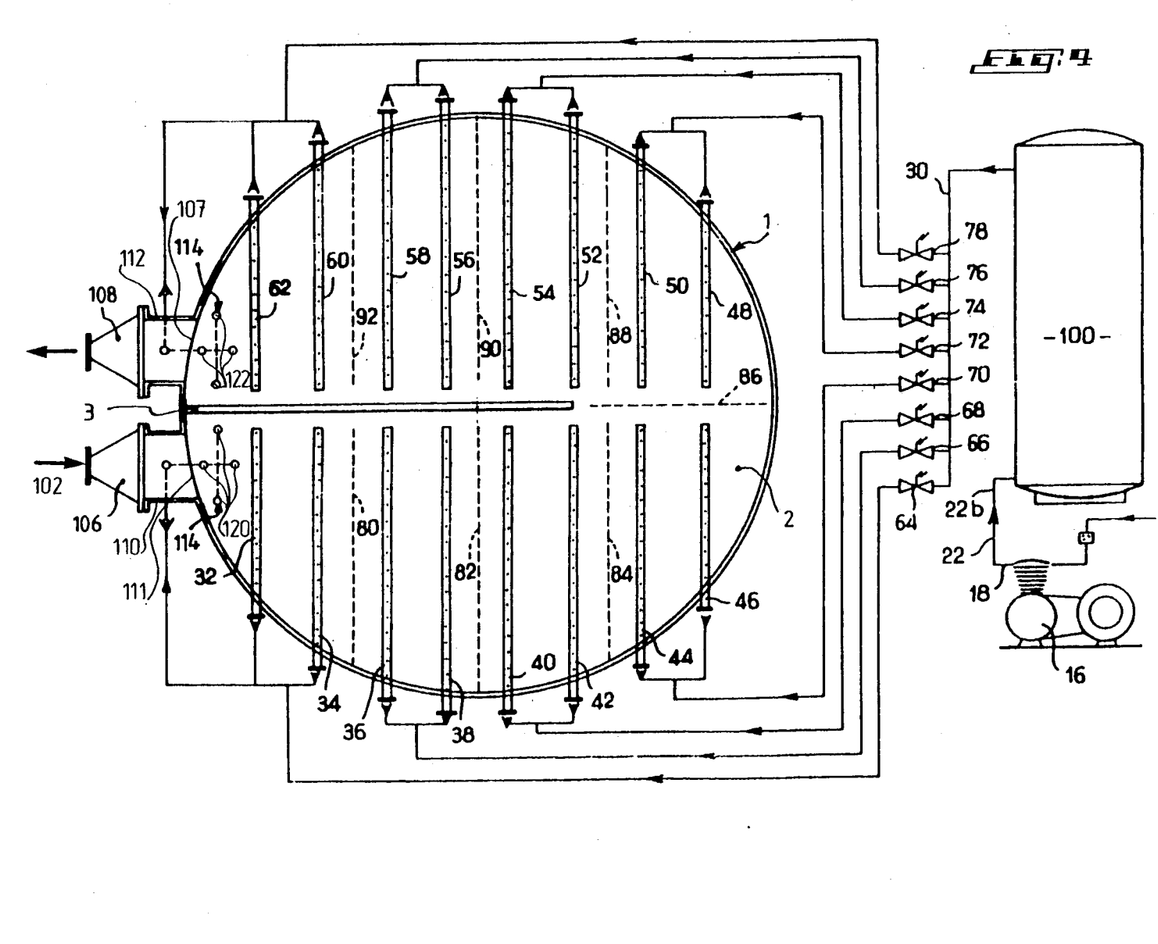
FIG. 4 shows an axial section of FIG. 3.

According to a variant forming the subject matter of FIGS. 3 and 4, the plant according to the invention comprises means 102 for the direct introduction of the products to be degraded through anaerobic fermentation, preferably towards the bottom of the vessel. These direct introduction means preferably comprise means for introduction through mechanical thrust advantageously comprising at least one pump for thick material 102 for the fermented products.

Such pumps for thick materials are presently available on the market and may constituted for instance by concrete pumps. Preferably the pump for thick material which is used is of the piston or screw type.

According to this alternative embodiment, the pump 102 would feed through a duct 104 which may be fitted with a valve 105, preferably a connected section 110 communicating with the inlet port proper 111 leading into the vat or vessel 2.

The provision of this connecting section allows to ensure a perfect fluid tightness between the direct introduction means 102 and the inside of the vat 2.

According to this alternative embodiment, the port 111 is disposed at a predetermined distance from the bottom of the vat 2.

On the other hand, the outlet port 107 for the degraded products from the vessel is preferably arranged in tangential relationship with the bottom of the vat so as to provide for an egress of the degraded products through gravity.

It should be noted that according to the present invention, the bottom of the vat may be sloping or substantially horizontal taking into account that the circulation of the products within the vat or vessel 2 is performed by the direct introduction means which carry out an introduction under pressure due to the mechanical thrust.

Likewise, one provides a connecting section 112 at the outlet 107 so as to also achieve the fluid-tightness between the outside and the inside of the vessel 2 in order not to disturb the fermentation taking place inside of the vessel 2.

According to a particularly advantageous characteristic of the present invention, one interposes between the introduction means 102 and the inlet 111 of the vat 2, preferably between the means 102 and the connecting section 110, a divergent device 106 preferably in the shape of a frustum of a cone, the big base of which is connected to the connecting section 110 of suitable size so as to facilitate the ingress of the products into the fermentation vessel or vat and to promote a gradual advancing motion of the material present within the vessel owing to the thrust front.

Likewise, one preferably disposes at the outlet of the products from the vessel 2 a convergent device 108 which promotes the egress of the digestate for instance in recuperator piping 116 (FIG. 3) and its being thrown towards a press symbolized by the reference numeral 118.

It should be noted that according to this alternative embodiment, the distribution and subdivision of the biogas is carried out as in the embodiment forming the subject matter of FIGS. 1 and 2.

According to a preferred characteristic, one also provides stirring means 114 at the inlet and preferably also at the outlet of the vat 2 so as to carry out a stirring with the biogas consistent in terms of volume and time with the density of the product to be degraded. This stirring may be carried out immediately or in proximity of the inlet port 111 or the outlet port 107.

These stirrings are carried out in accordance with the cycle described with reference to FIGS. 1 and 2 and may therefore be either regularly repeated or not with a well adapted gas volume and this through the medium of the compressor 16 and of the buffer tank 100.

Figure 5:
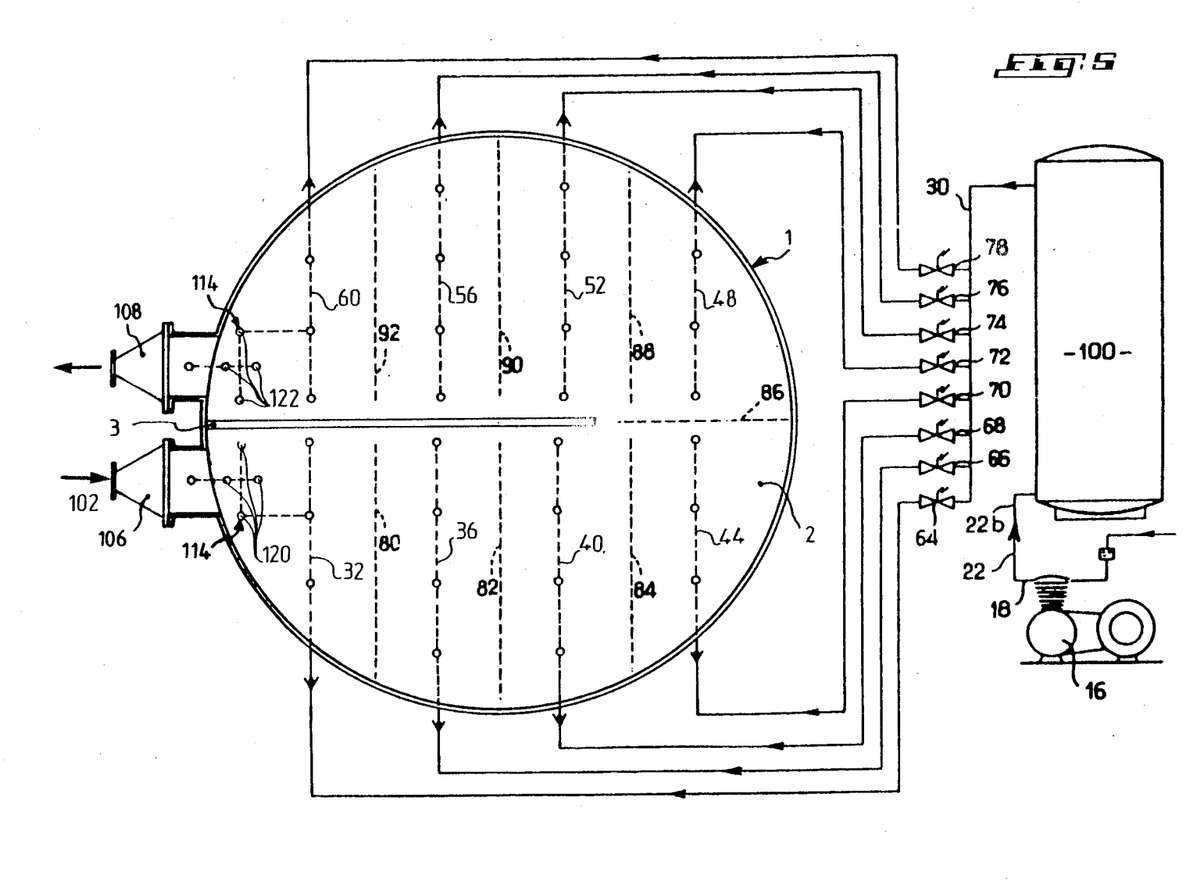
FIG. 5 shows an alternative embodiment for the reintroduction of the biogas.

According to the alternative embodiment forming the subject matter of FIG. 5, the stirring means 114 are provided in branched-off relationship with the biogas reintroduction duct 32 or 60, this branching-off being inside of the vessel 2. This branching-off may comprise several biogas outlet ports 120 or 122 according to the embodiment of FIG. 4, this branching-off is provided outside of the vat 2.

Also according to the embodiment of FIG. 5, each sector independently fed with biogas may comprise one single biogas reintroduction duct 32, 36, 40, 44, 48, 52, 56, 60 only. Naturally, as with the embodiment of FIG. 4, one may provide two or more biogas reintroduction ducts.

It will thus be understood that this equipment operates according to the method previously described and that one obtains an improvement of the method comprising an improvement of the equipment while carrying out a perfect and homogeneous fluidizing of the solid products or substrates within the vat 2.

On the other hand, according to the variant of FIGS. 3 to 5, one obtains a direct introduction of the products while allowing operation in an anerobic manner at atmospheric pressure while avoiding extra costs due to the manufacture of vats capable of withstanding working pressure above 1 bar and by simultaneously solving the problem of fluid tightness, in particular by the provision of connecting sections forming a tight plug of material allowing to avoid disturbing the fermentation.

I claim:

1. Method for carrying out a methanogenesis of organic products, by-products and waste of human, animal and vegetable origin, resulting in the production of degraded products and biogas and comprising feeding a mass of products to be degraded into a closed fermentation vessel comprising an inlet and an outlet, imposing upon said products a direction of circulation within said vessel from said inlet to said outlet, recovering produced biogas evolved above said mass of products and discharging the degraded products with a reintroduction of the biogas into the mass of products present within the vessel from the bottom of the vessel in order to produce a fluidization effect of said products, comprising the steps of subdividing said vessel into a plurality of different product density sectors juxtaposed in the direction of circulation, and injecting the biogas intermittently into each one of said sectors under a predetermined injection pressure and for a predetermined period of time, said pressure and period of time being selectively adjustable in each sector in accordance with the density of the products therein.

2. Method according to claim 1, wherein said biogas is injected into each sector successively in a time-shifted manner so as to achieve a rotation of the injection of biogas within the vessel from one sector to the other one.

3. Method according to claim 1, wherein a tank is provided for storing biogas under high pressure upstream of the fermentation vessel, the pressure being at least equal to the injection pressure in the sector having the highest density.

4. Method according to claim 1, wherein the injection is programmed by being also automatically interlocked with the detection of a lack of fluidity.

5. Method according to claim 1, wherein a pneumatic thrust is effected at the inlet of the vessel at the same time as the operation of the opening of a valve for discharging the biogas produced within the vessel whereas the pneumatic thrust is effected at the outlet of the vessel at the same time as the injection of biogas at a top of the vessel.

6. Method according to claim 1, wherein a direct introduction is effected into the vessel of the products to be degraded towards a bottom of said vessel at a predetermined distance from said bottom.

7. Method according to claim 6, wherein the direct introduction is carried out through a mechanical thrust whereas an egress is carried out through gravity.

8. Method according to claim 7, wherein the mechanical thrust is produced by a pump for thick material.

9. Method according to claim 8, wherein the pump is a piston pump.

10. Method according to claim 8, wherein the pump is a screw pump.

11. Method according to claim 1, wherein a stirring with biogas is carried out immediately at or in the vicinity of the inlet or outlet ports of the products into or out of the vessel.

12. The method of claim 1, additionally comprising seeding said products with a suitable substrate prior to the feeding thereof into the vessel.

13. Equipment for carrying out a methanogenesis of organic products, by-products and waste of human, animal and vegetable orign, of the kind comprising a reactor comprising an inlet for products and an outlet for fermented products and having an anaerobic fermentation vessel divided vertically into two parts, a first part being connected to the inlet for the products into said vessel, the second part being connected to the outlet for the fermented products, a biogas outlet, said equipment comprising a plurality of ducts (32 to 62) fluidly connected to the biogas outlet and forming a circuit for reinjecting the biogas into the fermentation vessel (2), sidewise spaced from each other and disposed at least in the major portion of the vessel (2), said ducts being fed with biogas individually or in groups through independent valves (64 to 78) so as to thus subdivide the fermentation vessel (2) into sectors independently fed with biogas, said equipment further comprising a programmed device (130) for controlling each valve (64 to 78) of each sector for the injection of biogas into each sector successively in a time-shifted manner and for controlling biogas pressure through each valve which is a function of density of the products in the sector involved.

14. Equipment according to claim 13, wherein the biogas injection circuit comprises a container (100) for storing biogas under pressure in which the biogas is stored until the building up of a pressure at least equal to the highest pressure required in one of the sectors of the vessel (2).

15. Equipment according to claim 14, wherein the biogas injection circuit comprises a duct (20b) for injecting biogas at a top of the fermentation vessel (2), comprising a valve proper (26) for producing a pneumatic thrust in the fermentation vessel (2).

16. Equipment according to claim 13, said equipment comprising means (102) for a direct introduction of the products to be degraded into the vessel towards a bottom of the vessel and at a predetermined distance from said bottom.

17. Equipment according to claim 16, wherein the direct introduction means (102) comprise means for producing a mechanical thrust comprising at least one pump for thick material.

18. Equipment according to claim 17, wherein the pump is a piston pump.

19. Equipment according to claim 17, wherein the pump is a screw pump.

20. Equipment according to claim 16, said equipment comprising a connecting section between the direct introduction means (102) and the inlet (111) of the vessel (2).

21. Equipment according to claim 13, said equipment comprising stirring means (114) immediately at or in the vicinity of the inlet (111) of the vessel.

22. Equipment according to claim 21, wherein the inlet of the vessel is provided with a divergent device (106) facilitating an ingress of the products in relation to the vessel (2).

23. Equipment according to claim 13, said equipment comprising stirring means (114) immediately at or in the vicinity of the outlet (107) of the vessel.

24. Equipment according to claim 23, wherein the outlet of the vessel is provided with a convergent device (108) facilitating an egress of the products in relation to the vessel (2).

25. Equipment according to claim 13, wherein the outlet of the products is substantially at a periphery of a bottom of the vessel.

26. The equipment of claim 13, wherein the biogas outlet is connected to a container forming a gasometer through a valve.

* * * * *